US00PP16346P2

(12) United States Plant Patent
van Elderen

(10) Patent No.: US PP16,346 P2
(45) Date of Patent: Mar. 14, 2006

(54) *ASTILBE* PLANT NAMED 'PINK JEWEL'

(50) Latin Name: *Astilbe simplicifolia*
Varietal Denomination: Pink Jewel

(75) Inventor: Renier van Elderen, Lijnden (NL)

(73) Assignee: Green Works International B.V., 't Zand (NL)

( * ) Notice: Subject to any disclaimer, the term of this patent is extended or adjusted under 35 U.S.C. 154(b) by 42 days.

(21) Appl. No.: 11/097,675

(22) Filed: Mar. 31, 2005

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP11,860 P2 * 5/2001 van Buren ..... Plt./263
PP14,933 P2 * 6/2004 Verduin ..... Plt./263
PP14,964 P2 * 6/2004 Verduin ..... Plt./263

OTHER PUBLICATIONS

UPOV ROM GTITM Computer Database, GTI Jouve Retrieval Software 2005/02 Citation for 'Pink Jewel'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Astilbe* plant named 'Pink Jewel', characterized by its upright, mounded and compact plant habit; rapid growth rate; freely and uniform flowering habit; and light red purple-colored flowers arranged on arching inflorescences.

1 Drawing Sheet

Botanical designation: *Astilbe simplicifolia.*
Cultivar denomination: 'Pink Jewel'.

BACKGROUND OF THE INVENTION

The present Invention relates to a new and distinct cultivar of *Astilbe* plant, botanically known as *Astilbe simplicifolia,* and hereinafter referred to by the name 'Pink Jewel'.

The new *Astilbe* is a product of a planned breeding program conducted by the Inventor in Lijnden, The Netherlands. The objective of the breeding program was to develop new fast-growing and compact *Astilbe* cultivars.

The new *Astilbe* originated from a chance pollination of two unknown *Astilbe simplicifolia* selections in 1996. The new *Astilbe* was discovered and selected by the Inventor as a single flowering plant originating from a group of open-pollinated crosses made in a controlled environment in Lijnden, The Netherlands in 1999 on the basis of its arching inflorescences and light red purple-colored flowers.

Asexual reproduction of the new cultivar by root divisions since 2000 in Lijnden, The Netherlands, has shown that the unique features of this new *Astilbe* are stable and reproduced true to type in successive generations.

SUMMARY OF THE INVENTION

Plants of the cultivar Pink Jewel have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Jewel'. These characteristics in combination distinguish 'Pink Jewel' as a new and distinct *Astilbe* cultivar:

1. Upright, mounded and compact plant habit.
2. Rapid growth rate.
3. Freely and uniformly flowering habit.
4. Light red purple-colored flowers arranged on arching inflorescences.

Plants of the new *Astilbe* can be compared to the *Astilbe* cultivar Sprite, not patented. In side-by-side comparisons conducted in Lijnden, The Netherlands, plants of the new *Astilbe* differed from plants of the cultivar Sprite in the following characteristics:

1. Plants of the new *Astilbe* grew faster than plants of the cultivar Sprite.
2. Plants of the *Astilbe* and the cultivar Sprite differed in inflorescence form and flower coloration.

Plants of the new *Astilbe* can also be compared to the *Astilbe* cultivar Inshriach Pink, not patented. In side-by-side comparisons conducted in Lijnden, The Netherlands, plants of the new *Astilbe* differed from plants of the cultivar Inshriach Pink in the following characteristics:

1. Plants of the new *Astilbe* had darker green-colored leaves than plants of the cultivar Inshriach Pink.
2. Plants of the new *Astilbe* and the cultivar Inshriach Pink differed in inflorescence form and flower coloration.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the actual colors of the new *Astilbe.* The photograph comprises a side perspective view of a typical flowering plant of 'Pink Jewel' grown in a container.

DETAILED BOTANICAL DESCRIPTION

Plants shown in the aforementioned photograph and used in the following description were grown in 17-cm containers under conditions which closely approximate commercial production conditions during the summer in an outdoor nursery in Lijnden, The Netherlands. Plants were about one year old when the photographs and description were taken. During the production of the plants, day temperatures ranged from 5° C. to 20° C. and night temperatures ranged from 2° C. to 12° C. In the following description, color references are made to The Royal Horticultural Society Colour Chart, 1995 Edition, except where general terms of ordinary dictionary significance are used.

Botanical classification: *Astilbe simplicifolia* cultivar Pink Jewel.

Parentage:

*Female, or seed, parent.*—Unknown selection of *Astilbe simplicifolia.*

*Male, or pollen, parent.*—Unknown selection of *Astilbe simplicifolia.*

Propagation:

*Type.*—By root divisions.

*Time to initiate rooting, summer.*—About 30 days at 18° C.

*Time to initiate rooting, winter.*—About 40 days at 18° C.

*Time to produce a rooted young plant.*—About 25 weeks at 18° C.

*Root description.*—Fine.

Plant description:

*Form.*—Perennial. Upright, mounded and compact plant habit; inverted triangle. Flowering stems and leaves arise from the roots; dense and bushy plant habit; moderately vigorous growth habit. Freely flowering with numerous flowers on numerous branched panicles.

*Growth rate.*—Rapid; from divisions, about 25 weeks are required to produce fully-grown flowering plants in 17-cm containers.

*Plant height.*—About 30 cm.

*Plant width.*—About 30 cm.

*Stem description.*—Length: About 25 cm. Diameter: About 5 mm. Internode length: About 5 cm. Strength: Strong. Texture: Sparsely pubescent. Color: 139A.

*Foliage description.*—Arrangement: Alternate; bi-ternately compound. Leaf length (including petiole): About 20 cm. Leaf width: About 15 cm. Leaflet length: About 5 cm. Leaflet width: About 2.5 cm. Leaflet shape: Ovate to elliptic. Leaflet apex: Acuminate to acute. Leaflet base: Cuneate to oblique. Leaflet margin: Serrate or occasionally bis-errate. Leaflet texture, upper and lower surfaces: Sparsely pubescent. Leaflet luster, upper and lower surfaces: Slightly lustrous. Leaflet venation pattern: Pinnate. Leaflet color: Developing and fully expanded foliage, upper surface: 139A; venation, 146D. Developing and fully expanded foliage, lower surface: 146B; venation, close to 145B. Petiole length: About 15 cm. Petiole diameter: About 2.5 mm. Petiole texture, upper and lower surfaces: Smooth, glabrous. Petiole color, upper and lower surfaces: 184A; towards the stem, 153B.

Flower description:

*Flower arrangement and shape.*—Small single flowers arranged in arching branched panicles; flowers face upright, outward or droop. Freely and uniformly flowering habit; about 1,000 flowers and flower buds per plant.

*Natural flowering season.*—Continuous flowering during the summer in The Netherlands.

*Flower longevity on the plant.*—Individual flowers last several weeks on the plant and about one week as a cut flower. Flowers persistent.

*Fragrance.*—Faint; musty, but not unpleasant.

*Flower buds.*—Length: About 2 mm. Diameter: About 1.8 mm. Shape: Ovate to orbicular. Color: 64B.

*Flowers.*—Diameter: About 8 mm. Depth (height): About 4 mm.

*Petals.*—Quantity per flower: About five. Length: About 4 mm. Width: About 2 mm. Shape: Ligulate to linear. Apex: Obtuse. Margin: Entire. Texture, upper and lower surfaces: Smooth, glabrous. Color: When opening, upper and lower surfaces: 63C. Fully opened, upper and lower surfaces: 63C.

*Sepals.*—Quantity per flower: About five. Length: About 5 mm. Width: About 6 mm. Shape: Ovate. Apex: Obtuse. Base: Cuneate, fused. Margin: Entire. Texture, upper and lower surfaces: Smooth, glabrous. Color: Immature, upper and lower surfaces: 56D. Mature, upper and lower surfaces: 56D.

*Reproductive organs.*—Stamens: Quantity per flower: About ten. Anther attachment: Basifixed. Anther shape: Oblong. Anther length: Less than 0.5 mm. Anther color: 65C. Pollen amount: Scarce. Pollen color: 11D. Pistils: Quantity per flower: Two. Pistil length: About 2 mm. Stigma shape: Club-shaped. Stigma color: Close to 63C. Style length: About 1.5 mm. Style color: Close to 63C. Ovary color: Close to 63C.

*Seeds.*—Length: Less than 0.5 mm. Diameter: Less than 0.5 mm. Color: Light brown.

Disease/pest resistance: Plants of the new *Astilbe* have not been noted to be resistant to pathogens and pests common to *Astilbe.*

High temperature tolerance: Plants of the new *Astilbe* have been observed to tolerate temperatures of 30° C.

Hardiness: Plants of the new *Astilbe* are hardy to USDA Zone 5.

It is claimed:

1. A new and distinct cultivar of *Astilbe* plant named 'Pink Jewel', as illustrated and described.

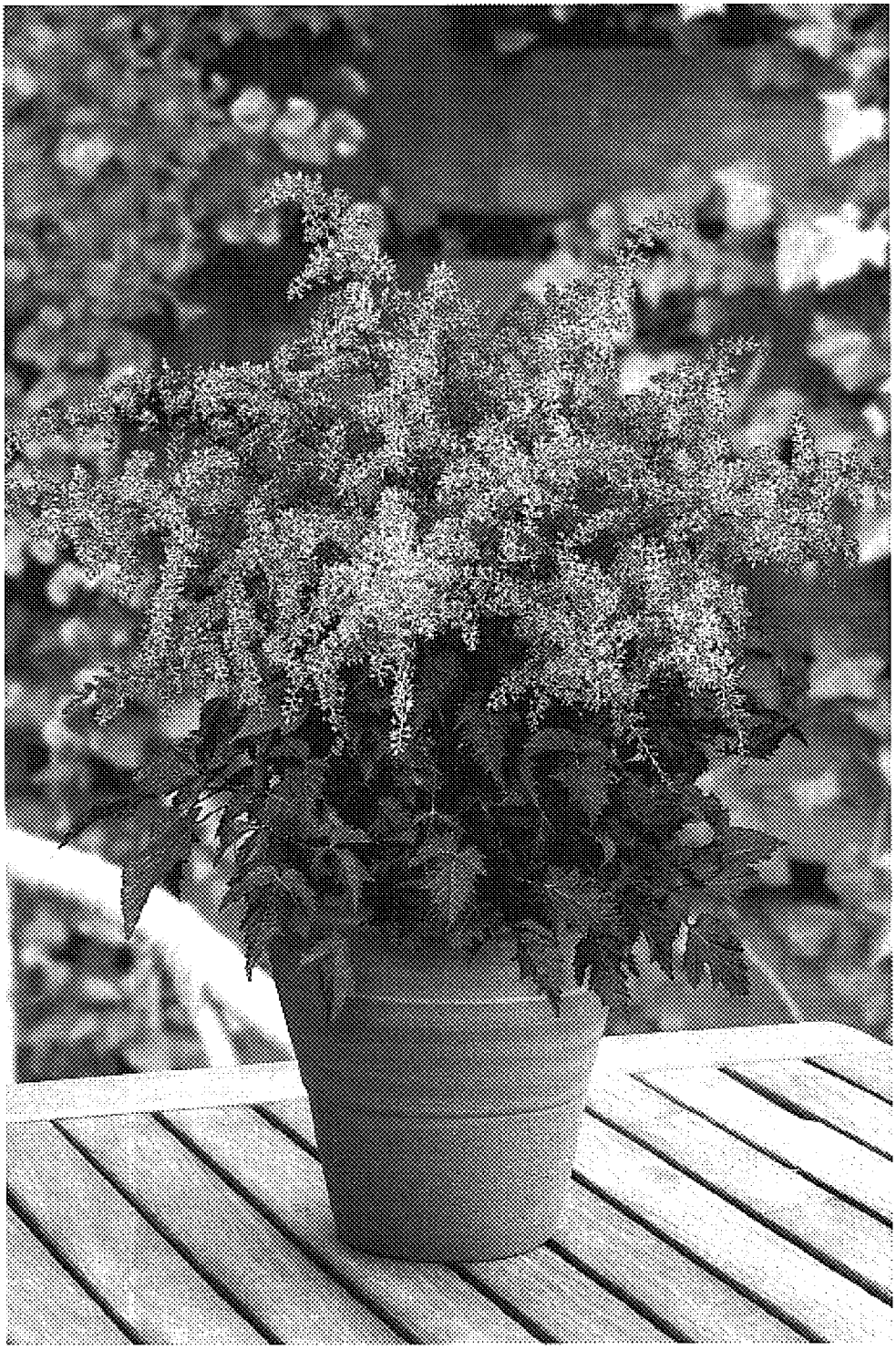

* * * * *